United States Patent
Kariv

(10) Patent No.: US 8,600,480 B2
(45) Date of Patent: Dec. 3, 2013

(54) SYSTEM AND METHOD FOR ASSESSING INTERFERENCE TO A SIGNAL CAUSED BY A MAGNETIC FIELD

(75) Inventor: Itay Kariv, Haifa (IL)

(73) Assignee: MediGuide Ltd., Haifa (IL)

( * ) Notice: Subject to any disclaimer, the term of this patent is extended or adjusted under 35 U.S.C. 154(b) by 871 days.

(21) Appl. No.: 12/650,739

(22) Filed: Dec. 31, 2009

(65) Prior Publication Data

US 2011/0156700 A1    Jun. 30, 2011

(51) Int. Cl.
*A61B 6/00* (2006.01)

(52) U.S. Cl.
USPC .......................................................... 600/424

(58) Field of Classification Search
USPC ............................. 324/228–263; 600/407–735
See application file for complete search history.

(56) References Cited

U.S. PATENT DOCUMENTS

| | | | |
|---|---|---|---|
| 6,233,476 B1 | 5/2001 | Strommer et al. | |
| 6,493,573 B1 | 12/2002 | Martinelli et al. | |
| 6,498,944 B1 | 12/2002 | Ben-Haim et al. | |
| 6,788,967 B2 | 9/2004 | Ben-Haim et al. | |
| 6,895,267 B2 | 5/2005 | Panescu et al. | |
| 6,937,906 B2 | 8/2005 | Terry et al. | |
| 7,197,354 B2 | 3/2007 | Sobe | |
| 7,263,397 B2 | 8/2007 | Hauck et al. | |
| 7,386,339 B2 * | 6/2008 | Strommer et al. | 600/424 |
| 7,933,727 B2 * | 4/2011 | Taulu et al. | 702/69 |
| 8,140,145 B2 * | 3/2012 | Kimura et al. | 600/424 |
| 8,362,762 B2 * | 1/2013 | Hokari | 324/244.1 |
| 8,380,289 B2 * | 2/2013 | Zellers et al. | 600/426 |
| 8,391,956 B2 * | 3/2013 | Zellers et al. | 600/426 |
| 8,446,147 B2 * | 5/2013 | Chiba et al. | 324/207.15 |
| 8,473,026 B2 * | 6/2013 | Ferre et al. | 600/407 |
| 2005/0083049 A1 * | 4/2005 | Brune et al. | 324/232 |
| 2007/0177414 A1 * | 8/2007 | Funato et al. | 365/36 |

* cited by examiner

*Primary Examiner* — Joshua Benitez-Rosario
(74) *Attorney, Agent, or Firm* — Dykema Gossett PLLC

(57) ABSTRACT

The present invention is directed to a system and method for assessing interference to a signal caused by magnetic field. The system includes a magnetic field generator configured to generate a magnetic field. The system further includes a first magnetic field sensor configured to detect a magnetic field and to generate a first signal representative of the magnetic field detected thereby. The system still further includes a second magnetic field sensor. The second magnetic field sensor is configured to detect a magnetic field and to generate a second signal representative of the magnetic field detected by the second magnetic field sensor. The system yet still further includes a processor. The processor is configured to receive and process the second signal to determine whether said magnetic field detected by said second magnetic field sensor may cause distortion to said first signal, as well as the magnitude of such distortion.

15 Claims, 4 Drawing Sheets

SYSTEM AND METHOD FOR ASSESSING INTERFERENCE TO A SIGNAL CAUSED BY A MAGNETIC FIELD

BACKGROUND OF THE INVENTION a. Field of the Invention

The present invention relates to a system and method for assessing interference to a signal caused by a magnetic field. More particularly, in an exemplary embodiment, the present invention relates to a system and method for assessing interference to a positioning signal generated by a magnetic field-based medical positioning system caused by a magnetic field within which the medical positioning system operates.

b. Background Art

Systems and methods for determining and/or monitoring the positioning (i.e., position and orientation) of medical devices within the anatomy of a patient using magnetic fields are generally known in the art. A description of one such system can be seen by reference to U.S. Pat. No. 7,386,339 entitled "Medical Imaging and Navigation System" to Strommer et al., the disclosure of which is incorporated herein by reference in its entirety. Strommer et al. disclose a magnetic field-based medical positioning system (MPS) for ascertaining the position and orientation of one or more MPS sensors. More particularly, the MPS is configured to acquire positioning (localization) data (i.e., the position and orientation) of one or more MPS sensors located on or within a medical device or tool. The position and orientation of an MPS sensor may be based on capturing and processing signals received from the MPS sensor while in the presence of a controlled AC magnetic field. Accordingly, the MPS sensor(s) may comprise one or more magnetic field detection coil(s).

Known MPS systems, such as that referenced above, may include a magnetic transmitter assembly (MTA) and a magnetic processing core for determining position and orientation readings. The MTA is configured to generate a magnetic field(s) in and around a certain area or region of a patient's body, such as, for example, the chest cavity, in a predefined three-dimensional space. Each MPS sensor is configured such that when disposed within the magnetic field(s), it senses or detects one or more characteristics of the magnetic field(s), and generates a signal corresponding to the detected characteristic(s). The signal generated by the sensor is provided to the magnetic processing core, which is responsive to the generated signals and is configured to calculate three-dimensional position and orientation readings for each MPS sensor. Thus, the MPS enables real-time tracking of one or more MPS sensors in three-dimensional space, and therefore, the real-time tracking of the corresponding medical device or tool with which the one or more MPS sensors are associated.

These magnetic field-based systems are not without their drawbacks, however. For example, because the medical device or tool with which the MPS sensor is associated operates in an environment with a magnetic field-based MPS, it inherently operates in a volume with a relatively strong magnetic field generated by the MPS. As such, the magnetic field generated by the MTA, for example, or a parasitic magnetic field, may cause interference with the signals transmitted by the MPS sensor(s) to the processing core of the MPS. This interference may cause distortions in the transmitted signals, thereby potentially compromising the fidelity of the transmitted signal and potentially rendering the position and orientation determinations using the distorted signals unacceptably inaccurate.

One attempt to combat this interference and its effects has been to protect the positioning signal. More particularly, one conventional method of protecting the signal generated by the MPS sensor is to twist the conductors or wires used to connect the MPS sensor with the processing core into a twisted-pair. This arrangement of the conductors has a cancellation effect on the interfering magnetic field, thereby preventing, or at least substantially reducing, the distortion to the positioning signal. One inherent limitation to this technique or methodology is that there are places between the MPS sensor and the processing core where it cannot be applied. For example, in connection areas, such as, for example, in the handle or proximal portion of the medical device or tool wherein two segments of conductors (e.g., two segments of twisted-pair conductors) are connected via a connector, the twisted-pair cannot be used. If this connection area is disposed within a magnetic field, and the magnetic field is strong enough, it will interfere with the positioning signal as it travels therethrough, thereby distorting the signal.

Accordingly, there is a need for a system that will minimize and/or eliminate one or more of the above-identified deficiencies.

BRIEF SUMMARY OF THE INVENTION

The present invention is directed to a system and method for assessing interference to a signal caused by a magnetic field, such as, for example, a magnetic field generated by the system itself, a magnetic field generated by a magnetic field-based system in conjunction with which the system is used, or a parasitic magnetic field. In an exemplary embodiment, the system according to the present teachings includes a magnetic field generator configured to generate a magnetic field. The system further includes a first magnetic field sensor configured to generate a first signal representative of a magnetic field detected by the first magnetic field sensor.

The system still further includes a second magnetic field sensor. The second magnetic field sensor is configured to generate a second signal that is representative a magnetic field detected by the second magnetic field sensor. The system yet still further includes a processor. The processor is configured to receive and process at least the second signal to determine a magnitude of distortion that the magnetic field detected by the second magnetic field sensor may cause to the first signal.

In accordance with another aspect of the invention, a method of assessing interference to a first signal caused by a magnetic field is provided. In an exemplary embodiment, the method includes a first step of generating, by a magnetic field sensor, a second signal representative of a magnetic field detected by the magnetic field sensor. The method further includes a second step of receiving, by a processor, the second signal generated by the magnetic field sensor. The method still further includes a third step of processing, by the processor, the second signal generated by the magnetic field sensor to determine a magnitude of distortion that the magnetic field detected by the magnetic field sensor may cause to the first signal.

The foregoing and other aspects, features, details, utilities, and advantages of the present invention will be apparent from reading the following description and claims, and from reviewing the accompanying drawings.

DETAILED DESCRIPTION OF THE INVENTION

Figure 1:
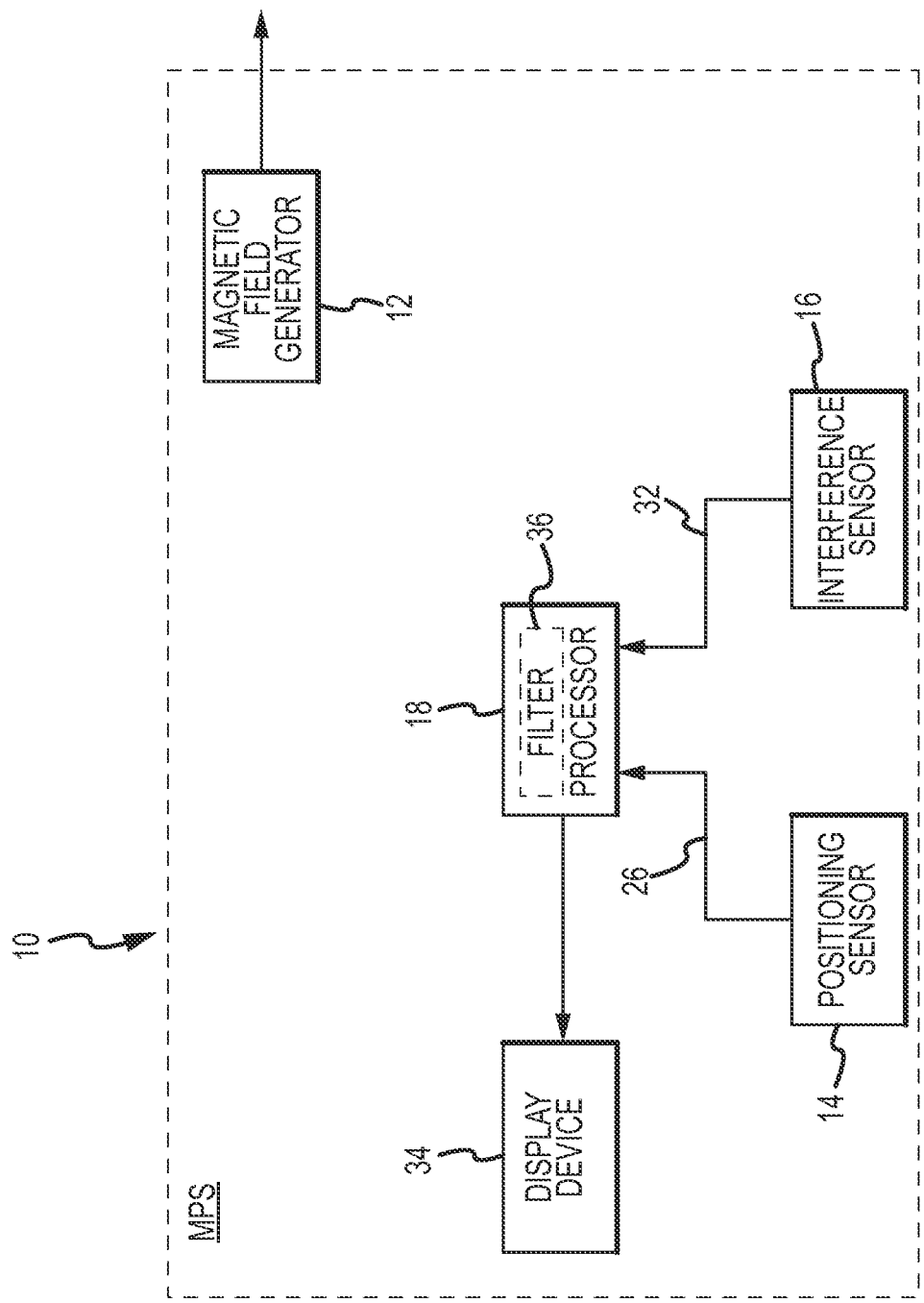
FIG. 1 is a schematic and block diagram view of an exemplary embodiment of a system for assessing interference to a signal caused by a parasitic magnetic field in accordance with the present teachings.

Referring now to the drawings wherein like reference numerals are used to identify identical components in the various views, FIG. 1 illustrates an exemplary embodiment of a system 10 for assessing interference to a signal caused by a magnetic field. In this illustrated embodiment, the system 10 may comprise, or be an integral part of, a magnetic field-based system. As illustrated in FIG. 1, in an exemplary embodiment, the system 10 includes, at least in part, a magnetic field generator 12, a first sensor 14, a second sensor 16, and a processor 18.

Figure 2:
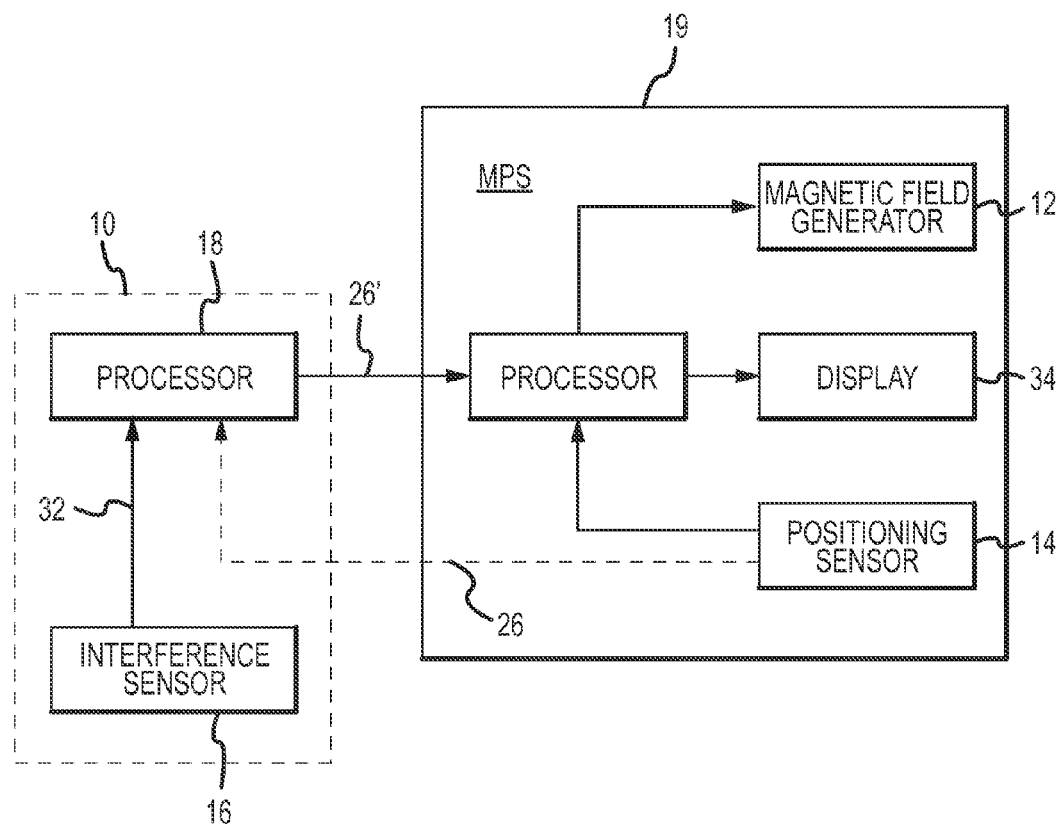
FIG. 2 is a schematic and block diagram view of another exemplary embodiment of the system illustrated in FIG. 1 in accordance with the present teachings.

FIG. 2 illustrates another exemplary embodiment of the system 10. In this illustrated embodiment, rather than comprising or being an integral part of a magnetic field-based system, the system 10 is a separate and distinct component that is used in conjunction with a magnetic field-based system (referenced as magnetic field-based system 19 in FIG. 2). Because this embodiment of the system 10 is separate and distinct from the magnetic-field-based system 19, it does not include all of the components of the embodiment illustrated in FIG. 1, such as, for example, the magnetic field generator 12. Accordingly, in this embodiment, the system 10 includes, at least in part, the second sensor 16 and the processor 18, wherein the processor 18 may be electrically connected to (via wires or wirelessly), and configured for communication with, the magnetic field-based system 19. Accordingly, the system 10 may take on any number of different arrangements and compositions, all of which remain within the spirit and scope of the present invention.

One example of a magnetic field-based system with which the system 10 is contemplated to be used in either embodiment described above is that of a magnetic field-based medical positioning system (MPS). One exemplary MPS with which the system 10 is contemplated to be used is the gMPS™ system commercially available from MediGuide Ltd., and as generally shown and described in U.S. Pat. No. 7,386,339 entitled "Medical Imaging and Navigation System," the disclosure of which was incorporated herein by reference above. Another exemplary magnetic field-based system with which the system 10 is contemplated to be used is the Carto™ system commercially available from Biosense Webster, and as generally shown and described in U.S. Pat. No. 6,498,944 entitled "Intrabody Measurement," and U.S. Pat. No. 6,788,967 entitled "Medical Diagnosis, Treatment and Imaging Systems," both of which are incorporated herein by reference in their entireties. It should be noted, however, that these specific systems are being provided for exemplary purposes only and that the present invention is not meant to be limited to use with only these particular systems, or the types of systems embodied thereby.

For ease of description purposes only, the system 10 will be described hereinafter as comprising, being an integral part or subsystem of, or being used in conjunction with, a magnetic field-based MPS. It should be noted, however, that the present invention is not meant to be limited to use with only a magnetic field-based MPS. Rather, the system 10 may find application with magnetic field-based systems other than a magnetic field-based MPS, or non-magnetic field-based systems (e.g., non-magnetic field-based MPS) that operate in concert or in conjunction with magnetic field generating systems.

With reference to FIG. 1, and as is generally known, the magnetic field generator 12 is configured to generate one or more controlled AC magnetic fields in and around a certain area or region of interest of a patient's anatomy in a pre-defined three-dimensional space. In one exemplary embodiment, and as will be described in greater detail below, the characteristics of the generated magnetic field are such that the field(s) may be used, in part, to acquire positioning data (i.e., position and orientation) of a magnetic field positioning sensor that is disposed within the generated magnetic field. By acquiring positioning data, the position and orientation of the positioning sensor and, if appropriate, a device or tool associated therewith, may be determined and monitored.

Figure 3:
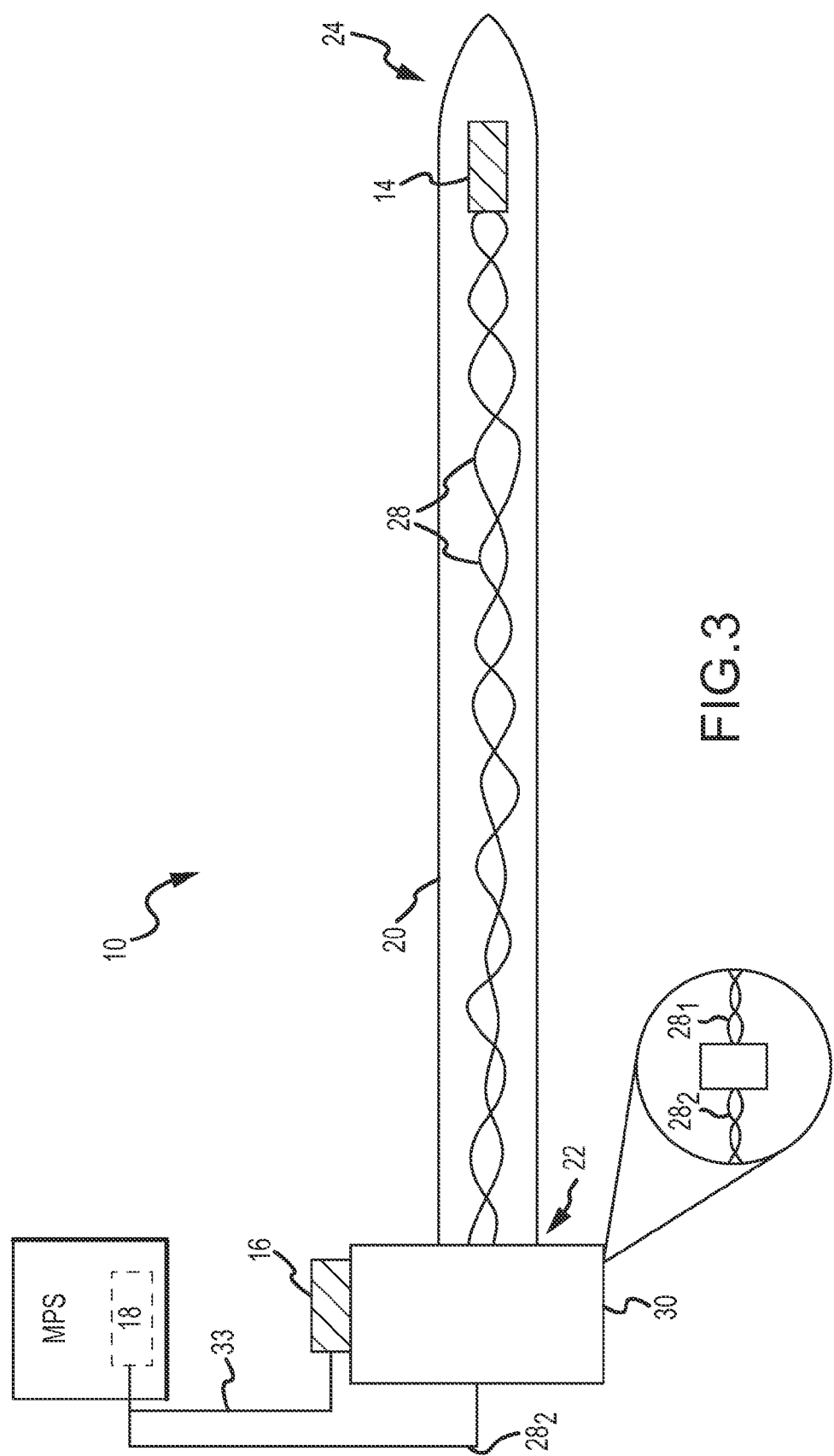
FIG. 3 is a diagrammatic view of the system illustrated in FIG. 1 in accordance with the present teachings.

With reference to FIG. 3, in an exemplary embodiment, the first sensor 14 comprises a positioning sensor, such as, for example, a MPS positioning sensor (positioning sensor 14). In such an embodiment, the positioning sensor 14 may take the form of any number of magnetic field sensors known in the art. For example, in one exemplary embodiment, the positioning sensor 14 comprises one or more magnetic field detection coil(s). For one example of a sensor, see U.S. Pat. No. 7,197,354 entitled "System for Determining the Position and Orientation of a Catheter," which is incorporated herein by reference in its entirety.

The positioning sensor 14 is configured to detect a magnetic field generated by the magnetic field generator 12, and to generate a signal 26 (hereinafter referred to as "positioning signal 26") representative of the detected magnetic field. More particularly, the positioning sensor 14 is configured to detect one or more characteristics of the magnetic field(s) in which it is disposed and to generate the positioning signal 26 that is indicative of the detected characteristic(s). In an embodiment wherein the positioning sensor 14 is a passive element (e.g., a magnetic field detection coil(s)), the positioning signal 26 comprises a signal induced in the coil(s) of the positioning sensor 14 by the surrounding magnetic field(s), and therefore, may be considered to be generated or produced by the positioning sensor 14. More particularly, the surrounding magnetic field(s) induce a current within the coil of the positioning sensor 14, which is interpreted as a voltage by the processor to which it is connected. The signal 26 may be used to determine the relative position and orientation of the positioning sensor 14 and, if appropriate, a medical device or tool with which the positioning sensor 14 is associated, within a given volume (i.e., the position and orientation of the sensor 14 and/or medical device within the heart or another anatomical structure of a patient).

Accordingly, the positioning sensor 14 is electrically connected to a processor of the MPS such that the positioning signal 26 is transmitted to the MPS for the position and orientation determination(s) to be made. In an embodiment wherein the processor 18 is part of the MPS (see FIG. 1, for example), the processor 18 may be configured to process positioning signal 26 and to make the position and orientation determination(s). Alternatively, a processor of the MPS other than the processor 18 may be configured to make the position and orientation determination(s) (see FIG. 2, for example). In an embodiment wherein the processor 18 is not part of the MPS, a processor within the MPS is configured to make the position and orientation determinations. The positioning sensor 14 may be electrically connected to the MPS (and, in an exemplary embodiment, to the processor 18) in a number of ways. In an exemplary embodiment, this connection is made through one or more wires 28. For example, as illustrated in FIG. 3 and as briefly described in the Background section above, this connection may be made by a pair of wires that are twisted to form a twisted-pair. However, one of ordinary skill in the art will appreciate that this electrical connection may be made using any number of electrical connection techniques, including hardwired and wireless connections.

As illustrated in FIG. 3, in an exemplary embodiment, the system 10 may further include, or at least be configured for use with, a medical device or tool (hereinafter collectively referred to as "medical device 20") that is designed for use and operation within a magnetic field environment, such as that generated by the magnetic field generator 12. In an exemplary embodiment, the medical device 20 may comprise, for example and without limitation, a catheter. The medical device 20 may be used in the performance of one or more medical procedures (e.g., mapping, imaging, navigation, therapy delivery, diagnostics, etc.).

In an exemplary embodiment wherein the system 10 includes or is configured for use with a medical device 20, the positioning sensor 14 is associated with the medical device 20. More particularly, the positioning sensor 14 may be mounted to or otherwise disposed within or on the medical device 20. In an exemplary embodiment wherein the medical device 20 is a catheter having a proximal end 22 and a distal end 24, the positioning sensor 14 is disposed at or near the distal end 24 of the catheter. In other exemplary embodiments, however, one or more positioning sensor(s) 14 may be disposed at one or more position(s) or location(s) throughout the medical device 20.

It should be noted that while the description above is directed primarily to an embodiment of the system 10 that includes a medical device with which the positioning sensor 14 is associated, in other exemplary embodiments, the system 10 may not include such a medical device or the positioning sensor 14 may not be associated with the medical device 20. Accordingly, the present invention is not limited to an embodiment wherein the system 10 includes a medical device with which the positioning sensor is associated, or in which the positioning sensor is associated with a medical device at all.

As briefly described above, and with continued reference to FIG. 3, the system 10 further includes the second sensor 16. In an exemplary embodiment, the second sensor 16 comprises an interference sensor (interference sensor 16). It should be noted that while the embodiment illustrated in FIG. 3 has one interference sensor 16, in other exemplary embodiments the system 10 may include multiple interference sensors 16. The interference sensor 16 may take the form of any number of magnetic field sensors known in the art. In one exemplary embodiment, the interference sensor 16 may comprise one or more magnetic field detection coil(s).

As with the positioning sensor 14, in an exemplary embodiment, the interference sensor 16 is configured to detect a magnetic field, such as, for example and without limitation, the magnetic field generated by the magnetic field generator 12, a magnetic field generated by a magnetic field generator other than the magnetic field generator 12, or a parasitic magnetic field. The interference sensor 16 is further configured to generate a signal 32 (hereinafter referred to as "interference signal 32") representative of the detected magnetic field. More particularly, the interference sensor 16 is configured to detect one or more characteristics of the magnetic field within which it is disposed, and to generate the interference signal 32 that is indicative of the detected characteristic(s). In an embodiment wherein the interference sensor 16 is a passive element (e.g., a magnetic field detection coil(s)), the interference signal 32 comprises a signal induced in the coil(s) of the interference sensor 16 by the surrounding magnetic field(s), and therefore, may be considered to be generated or produced by the interference sensor 16. More particularly, the surrounding magnetic field(s) induce a current within the coil of the interference sensor 16, which is interpreted as a voltage by the processor to which it is connected.

The interference signal 32 is used, at least in part, by the processor 18 to determine the magnitude of distortion that may be caused to the positioning signal 26 due to the interference resulting from the magnetic field detected by the interference sensor 16. When the positioning signal 26 is distorted, the position and orientation information determined using the data represented by the positioning signal 26, will also be distorted, and therefore, less than acceptably accurate. Accordingly, the system 10 is configured to determine the magnitude of distortion that may be caused to the positioning signal 26 and, as will be described in greater detail below, to alert the system operator of this fact, to provide information about the interference/distortion, and/or to compensate for the distortion.

As illustrated in FIGS. 1-3, the interference sensor 16 is electrically connected to the processor 18 such that the interference signal 32 generated by the interference sensor 16 is transmitted to the processor 18. Processor 18 is configured to evaluate the detected magnetic field represented by the interference signal 32 and to determine, for example, the distortion that may be caused to the positioning signal 26 by the magnetic field represented by the interference signal 32. The interference sensor 16 may be electrically connected to the processor 18 in a number of ways. In an exemplary embodiment, this connection is made through one or more wires 33 (e.g., a twisted-pair, for example). However, one of ordinary skill in the art will appreciate that this electrical connection may be made using any number of electrical connection techniques, including both hardwired and wireless connections.

In an exemplary embodiment such as that illustrated in FIG. 3, the interference sensor 16 is disposed apart from the positioning sensor 14. The interference sensor 16 may be located at any location within the system 10 along or near the path between the positioning sensor 14 and the MPS, and/or the processor 18, that is susceptible to magnetic field pickup (e.g., at a connection area or point wherein two segments of twisted-pair conductors (e.g., wires $28_1$ and $28_2$ in FIG. 3) are connected, for example). In an exemplary embodiment, the interference sensor 16 is associated with the medical device 20 that is part of or configured for use with the system 10. In the embodiment illustrated in FIG. 3 wherein the medical device 20 is a catheter, the interference sensor 16 may be disposed at or near the proximal end 22 of the catheter. More particularly, in an exemplary embodiment, the medical device 20 may include a connector 30 for connecting two twisted-pairs of conductors. In an exemplary embodiment, the interference sensor 16 is associated with the connector 30. More particularly, the interference sensor 16 may be mounted to or otherwise disposed on or within the connector 30. In another exemplary embodiment, the interference sensor 16 is not associated with the connector 30, but rather may be mounted to or otherwise disposed on or within the medical device 20 at a location other than at the connector 30 that is susceptible to magnetic field pick-up.

With reference to FIGS. 1-4, the processor 18 of the system 10 will now be described. As set forth above, the processor 18 may be a part of a MPS (i.e., the processor 18 may be configured to make position and orientation determinations in addition to the functionality described herein, or, in the alternative, may be a processor of the MPS separate and distinct from the processor that makes position and orientation determinations). Alternatively, the processor 18 may be separate and distinct from the MPS, and electrically connected to, and configured for communication with, the MPS. As such, the description above, and that to appear below, apply to either arrangement with equal force. As also described above, the processor 18 is electrically connected to at least the interference sensor 16, and in another exemplary embodiment, to both the interference sensor 16 and the positioning sensor 14.

The processor 18 is configured to receive the interference signal 32 generated by the interference sensor 16. The processor 18 is further configured to process the interference signal 32 to determine the magnitude of distortion that may be caused to the positioning signal 26 by the magnetic field detected by the interference sensor 16 and represented by the interference signal 32 (i.e., the interference generated or created by the detected magnetic field). In the exemplary embodiment wherein the processor 18 is electrically connected to both the interference sensor 16 and the positioning sensor 14, the processor 18 is configured to receive both the positioning and interference signals 26, 32, and to process the signals 26, 32 together to determine the distortion that may be caused to the positioning signal 26.

In an exemplary embodiment, the processor 18 is programmed with a predetermined magnetic field threshold value that represents the lowest strength magnetic field that could potentially cause unacceptable interference or distortion in or to the positioning signal 26. Alternatively, the threshold value could represent the highest strength magnetic field that can be tolerated without causing unacceptable interference or distortion to the positioning signal 26. In an exemplary embodiment, the value of this threshold is determined by bench testing or in practice, or could be determined during installation of the system 10. This threshold value may be fixed or may be adjustable by a user of the system 10. Accordingly, the processor 18 may be preprogrammed with the predetermined threshold, or alternatively, a user may input or exert a measure of control over the threshold value via a conventional I/O interface (e.g., keyboard, keypad, touch screen, mouse, and the like), thereby allowing the threshold value to be programmed and/or changed by the user.

As briefly described above, the predetermined threshold may be a value of the magnetic field that has been determined, either by way of experimentation or through practice, to be likely to cause unacceptable interference with, and therefore, distortion to, a signal generated by a sensor, such as, for example, a positioning sensor (i.e., positioning sensor 14). For instance, in an exemplary embodiment, the threshold value may correlate to a magnetic field value that would be expected to cause interference with, and therefore, distortion to, the positioning signal 26, thereby resulting in an error in the positioning determination made using the distorted positioning signal 26 that is outside of a certain degree of confidence. Accordingly, the positioning determination would be rendered unacceptably inaccurate. In other words, using the distorted signal, the MPS would determine a position and/or orientation of the medical device (i.e., the positioning sensor) that is inaccurate by an unacceptable distance (i.e., on the order of millimeters, for example) as a result of the interference caused by the magnetic field detected by the interference sensor 16. Alternatively, rather than deriving the threshold based on the value of the magnetic field that is likely to cause distortion to the signal that would result in an inaccurate positioning determination, in another exemplary embodiment, the threshold correlates to a magnetic field value that causes enough interference that the positioning signal is rendered undesirable to the MPS.

In the embodiment wherein the processor 18 is programmed with a magnetic field threshold value, the processor 18 receives the interference signal 32 from the interference sensor 16 and compares the value of the detected magnetic field strength represented by the interference signal 32 with the predetermined threshold value. If the value of the detected magnetic field is less than the threshold value, the processor 18 is configured to make the determination that the magnetic field detected by the interference sensor 16 will not, or at least not appreciably or unacceptably, interfere with or distort the positioning signal 26. As will be described in greater detail below, this determination, and/or the value of the magnetic field detected by the interference sensor 16, may be communicated to the user of the system 10 (or the MPS) in the form of, for example, an audio or visual display.

On the other hand, if the value of the magnetic field detected by the interference sensor 16 is equal to or greater than the threshold value, the processor 18 is configured to make the determination that the detected magnetic field will interfere with or distort the positioning signal 26. As will be described in greater detail below, in an exemplary embodiment, this determination, and/or the value of the magnetic field detected by the interference sensor 16, is communicated to the user of the system 10 (or the MPS) in the form of, for example, an audio or visual alert or display. As will also be described in greater detail below, in addition, or alternatively, the processor 18, or another component in the system 10 or the MPS, may compensate for the interference or distortion to the positioning signal 26 caused by the magnetic field detected by the interference sensor 16.

In another exemplary embodiment, rather than, or in addition to, comparing the value of the magnetic field detected by the interference sensor 16 with a predetermined threshold value, the processor 18 is configured to estimate the magnitude of distortion the interference from the detected magnetic field may cause to the positioning signal 26. In one embodiment, this estimation may be made based on the interference signal 32 alone. For example, the value of the magnetic field detected by the interference sensor 16 and represented by the interference signal 32 may be evaluated by the processor 18, and an estimated magnitude of distortion may be determined. This may done, for example, by looking up the value represented by the interference signal 32 in a look-up table stored on, or readily accessible by, the processor 18 and then associating the magnetic field detected by the interference sensor 16 with a corresponding magnitude of distortion. The magnitude of distortion may be, for example, a certain amount of voltage by which the positioning signal 26 is predicted to be distorted. In another exemplary embodiment, the estimation may be made by processing the positioning and interference signals 26, 32 together. More particularly, in this embodiment, the processor 18 receives both the positioning and interference signals 26, 32 from the respective sensors 16, 18 and processes them together to estimate the distortion caused to the positioning signal 26 as a result of the magnetic field detected by the interference sensor 16. In one exemplary embodiment, in general terms, the processor 18 "subtracts" the magnetic field or "noise" detected by the interference sensor 16 from the positioning signal 26 to estimate the amount or level of interference/distortion to which the positioning signal 26 is likely to be subjected by the magnetic field detected by the interference sensor 16. The processor 18 may be configured to use the result of the "subtraction" in a number of ways to estimate or otherwise determine the distortion caused to the positioning signal. For example, the result of the "subtraction" may be compared with a threshold, or used in conjunction with a look-up table to estimate the level of interference.

As with the embodiment described above, and as will be described in greater detail below, once the magnitude of distortion is estimated or determined, the system 10 may be configured to communicate to the user, for example and without limitation, whether the detected magnetic field will cause distortion, the level or likelihood of the predicted distortion (e.g., HIGH, MEDIUM, LOW, for example), and/or the estimated or determined magnitude of distortion to the positioning signal 26. In an exemplary embodiment, the system 10 may be configured to communicate to the user that that magnitude of distortion is so high that compensation techniques, such as those described in greater detail below, can not be used to correct or compensate for the distortion. In any event, this communication may be in the form of, for example, an audio or visual alert. As will also be described in greater detail below, in addition, or alternatively, the processor 18 or another component in the system 10 or the MPS, may compensate for the estimated interference or distortion to the positioning signal 26 caused by the magnetic field detected by the interference sensor 16.

As described above, in an exemplary embodiment, the system 10 may be configured to communicate to the user of the system 10 or the MPS certain information relating to the magnetic field detected by the interference sensor 16, such as, for example and without limitation, the strength of the detected magnetic field, an indication as to whether the detected magnetic field will cause distortion, the level or likelihood of the predicted distortion, the predicted magnitude of the distortion caused to the positioning signal 26, and an indication that the distortion is of such a magnitude that it cannot be compensated for. Accordingly, in an exemplary embodiment, the system 10 further includes a display device 34. The display device 34 may take the form of a visual display device (e.g., a computer monitor), an audio display device (e.g., a speaker), a combination of the two, or another display device known in the art. Additionally, the display device 34 may be part of the MPS or may be a separate and distinct component.

Accordingly, in view of the above, in an exemplary embodiment the processor 18 is configured to generate one or more signals representative of certain information relating to the magnetic field detected by the interference sensor 16. For example, in one embodiment, the processor 18 is configured to generate an alert signal that a detected magnetic field is likely to cause distortion to the positioning signal 26. In addition, or alternatively, the processor 18 may be configured to generate a signal corresponding to the strength or magnitude of the magnetic field detected by the interference sensor 16, and/or an indication as to the degree or magnitude of the distortion that is likely to be caused by the detected magnetic field. In another exemplary embodiment, rather than processor 18 generating these particular signals, another processor electrically connected to (i.e., via wires or wirelessly), and in communication with, the processor 18 (such as, for example and without limitation, a processor within the MPS in an embodiment wherein processor 18 is separate and distinct from the MPS) may be configured to generate the above described signals.

Whether the processor 18 or another processor is configured to generate the signals, the display device 34 is configured to be controlled by the processor generating the signals to display the information represented thereby. Accordingly, the user of the system 10 may be advised, for example and without limitation, as to whether the position and orientation information being generated or determined by the MPS is potentially inaccurate due to interference caused by a magnetic field detected by the interference sensor 16, the magnitude or level of the magnetic field detected by the interference sensor 16, the magnitude of the distortion likely to be caused due to the detected magnetic field, and that the distortion is of such a magnitude that it cannot be compensated for.

As briefly described above, and with reference to FIGS. 1 and 4, in an exemplary embodiment, the system 10 is additionally, or alternatively, configured to compensate for distortion to the positioning signal 26. In an exemplary embodiment, the system 10 includes a filter 36 configured to filter out or clean up the distortion in or to the positioning signal 26. The filter 36 may take the form of a conventional filter design, such as, for example, a noise cancellation filter, and/or may be implemented in hardware, software, and/or firmware. The filter 36 may be part of the MPS and/or the processor 18, or may be a separate and distinct component that communicates with the MPS and/or the processor 18. In an exemplary embodiment, the filter 36 is configured to receive as inputs the positioning and interference signals 26, 32, and to output a filtered signal 26' that is then used by the MPS to determine the position of the positioning sensor 14. In another exemplary embodiment, the determined or estimated magnitude of distortion may be provided to the filter 36 for use in generating the filtered signal 26'. Accordingly, by knowing the characteristics of the magnetic field detected by the interference sensor 16, filter designs using known signal processing tools can be used to improve the fidelity of the signals being used by the MPS to determine position and/or orientation of the positioning sensor 14, and therefore, the medical device 20.

Figure 4:
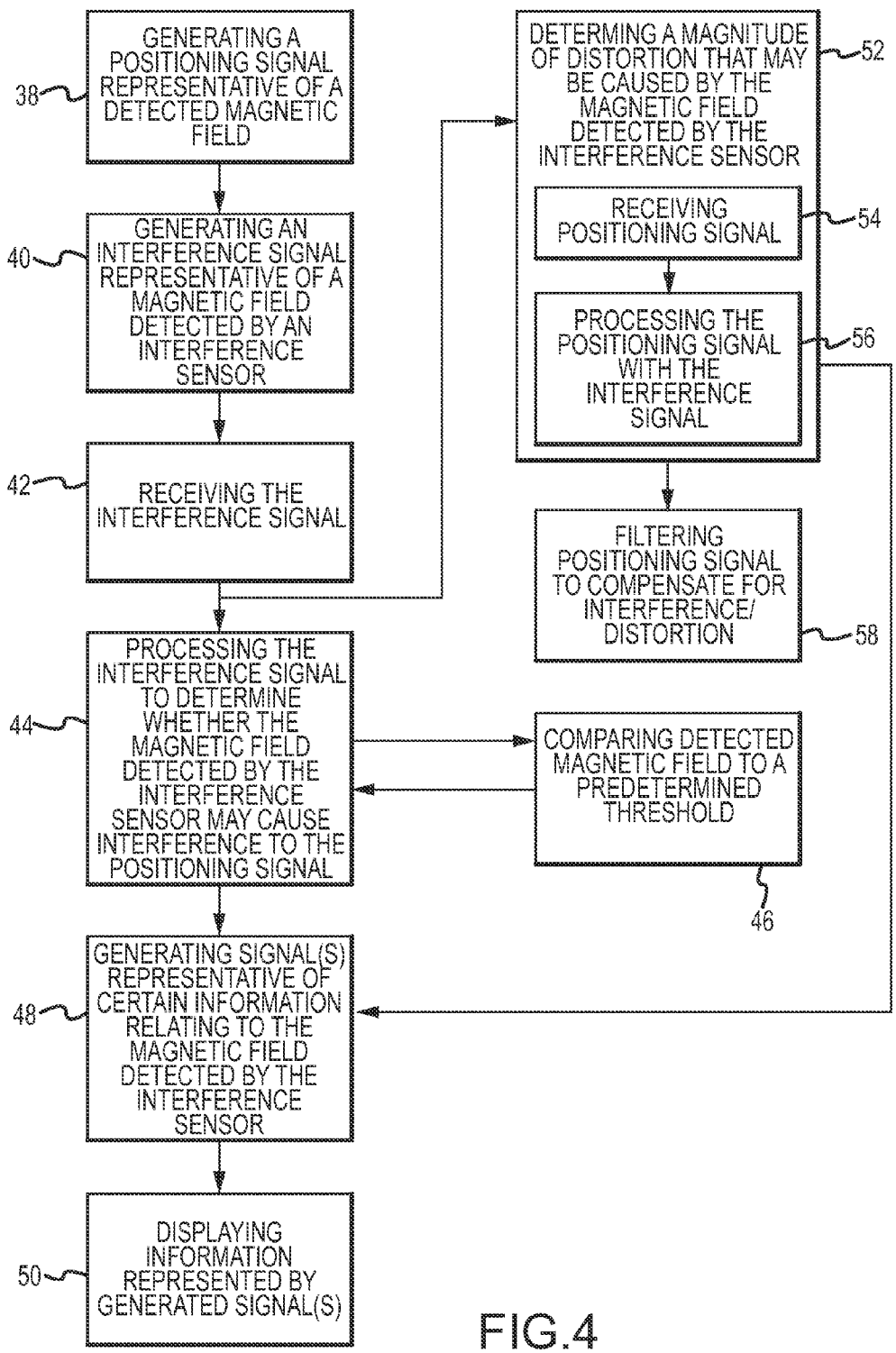
FIG. 4 is a flow chart illustrating an exemplary method of assessing interference to a signal caused by a parasitic magnetic field in accordance with the present teachings.

In accordance with another aspect of the invention, a method for assessing the interference to a signal caused by a magnetic field, such as, for example, a magnetic field generated by a magnetic field-based positioning system, a parasitic magnetic field, or any other magnetic field that may be detected, is provided. With reference to FIG. 4, in an exemplary embodiment, the method includes a first step 38 of generating, by the positioning sensor 14, the positioning signal 26 representative or indicative of a magnetic field detected by the positioning sensor 14. The method further includes a second step 40 of generating, by the interference sensor 16, the interference signal 32 representative or indicative of a magnetic field detected by the interference sensor 16. A third step 42 includes receiving, by the processor 18, the interference signal 32. In a fourth step 44, the processor 18 processes the interference signal 32 to determine the magnitude of distortion that may be caused to the positioning signal 26 due to the magnetic field detected by the interference sensor 16. In an exemplary embodiment, the processing step (step 44) includes the substep 46 of comparing the magnetic field detected by the interference sensor 16 to a predetermined "interfering" magnetic field threshold value. Alternatively, or additionally, the substep 46 may comprise looking up the detected magnetic field in a look-up table.

In an exemplary embodiment, the method further includes a fifth step 48 of generating one or more signals representative or indicative of certain information relating to the magnetic field detected by the interference sensor 16. In one exemplary embodiment, the generated signal is representative of an alert that the magnetic field detected by the interference sensor 16 is likely to cause distortion to the positioning signal 26. Alternatively, or in addition, the fifth step 48 may include generating a signal representative of, for example and without limitation, the level or magnitude of the magnetic field detected by the interference sensor 16, and/or the magnitude or degree of distortion to the positioning signal 26 that may be caused by the detected magnetic field. In a sixth step 50, the information represented by the signal(s) is displayed on a display device.

With continued reference to FIG. 4, in an exemplary embodiment, the method still further includes a seventh step 52 of estimating or determining a magnitude of distortion that may be caused by the magnetic field detected by the interference sensor 16. Step 52 may further include a first substep 54 of receiving, by the processor 18, the positioning signal 26, and a second substep 56 of processing the positioning and interference signals 26, 32 together to estimate the magnitude of distortion. In one exemplary embodiment, the seventh step 52 is itself a substep of the processing step 44.

In an exemplary embodiment, the method may yet still further include the eighth step 58 of filtering the positioning signal 26 to compensate for the distortion caused thereto by the magnetic field detected by the interference sensor 16. The filtered signal may then be transmitted to the MPS or, if the processor 18 is so configured, to the processor 18, for the calculation of positioning information (i.e., position and orientation) using the filtered signal.

It should be noted that other embodiments of the method described above may include fewer than all of the steps set forth above. For example, in an exemplary embodiment, the method may only include, for example, steps 40 (generating an interference signal), 42 (receiving, by the processor 18, the interference signal) and 44 (processing the interference signal to determine the magnitude of distortion that may be caused to the positioning signal 26). Accordingly, embodiments of the method including fewer than all of the above-described steps remain within the spirit and scope of the present invention.

It should be further noted that while the description above is directed primarily to a magnetic field-based positioning system application, the description applies with equal force to other magnetic field-based systems and/or other types of systems that operate in concert or in conjunction with magnetic field-based systems. For example, the system 10, in one form or another, may find application in imaging systems; visualization, mapping, and navigation systems; electroanatomical mapping systems; and the like that may be deployed in connection with magnetic field-based systems. Accordingly, it is contemplated that the system 10, and the principles thereof described above may find application in conjunction with systems such as, for example, the EnSite NavX™ System commercially available from St. Jude Medical, Inc. and as generally shown with reference to U.S. Pat. No. 7,263,397 entitled "Method and Apparatus for Catheter Navigation and Location and Mapping in the Heart," the disclosure of which is incorporated herein by reference in its entirety. Similarly, while the description above is directed primarily to an embodiment wherein the first sensor 14 is a positioning sensor, the present invention is not meant to be so limited. Rather, other sensors, whether magnetic field-based or otherwise, that generate signals within an MPS or another system operating within, or at least in close proximity to, a magnetic field-based system and that, as such, may be subjected to interference caused by a magnetic field, may also comprise the first sensor 14.

Although only certain embodiments of this invention have been described above with a certain degree of particularity, those skilled in the art could make numerous alterations to the disclosed embodiments without departing from the scope of this disclosure. For example, the system may be part of a larger MPS, or may be a separate and distinct component that may communicate with an MPS. Further, the signal generated by the first sensor may be a positioning signal or a signal other than a positioning signal that is generated by a sensor other than a positioning sensor. Still further, the signal generated by the first sensor may be filtered in any number of ways using any number of techniques. Still further, the system may be configured to display any number of types of information relating to the magnetic field detected by the interference sensor and the distortion resulting from such interference. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

What is claimed is:

1. A system for assessing interference to a first signal within a transmission line, the interference caused by a magnetic field, comprising:
   an interference sensor configured to detect said magnetic field and to generate a second signal representative of said magnetic field; and
   a processor electrically connected to said interference sensor and configured to process said second signal to determine whether said magnetic field may cause distortion to said first signal within said transmission line,
   wherein said processor is configured to determine a magnitude of distortion likely to be caused to said first signal by said magnetic field.

2. The system of claim 1, wherein said processor is configured to generate a third signal representative of certain information relating to said magnetic field; said system further comprising a display device wherein said processor is configured to control said display device to cause said information represented by said third signal to be displayed.

3. The system of claim 1, wherein said processor is configured to receive said first signal and to process said first and second signals together to determine said magnitude of distortion.

4. The system of claim 1 further comprising a filter to compensate for the distortion caused to said first signal by said magnetic field.

5. The system of claim 1, wherein said magnetic field is a first magnetic field, the system further comprising:
   a magnetic field generator configured to generate a second magnetic field; and
   a first magnetic field sensor configured to generate said first signal, wherein said first signal is representative of said second magnetic field as detected by said first magnetic field sensor.

6. The system of claim 5 further comprising a device configured for use within said second magnetic field, and wherein said first magnetic field sensor is associated with said device.

7. The system of claim 6 wherein said device includes a connector for connecting two segments of conductors, said transmission line comprising said connector and one or both of said segments of conductors, and wherein said interference sensor is associated with said connector.

8. The system of claim 5, wherein said processor is configured to compare said first magnetic field as detected by said interference sensor with a predetermined magnetic field threshold value to determine whether said first magnetic field may cause interference to said first signal within said transmission line.

9. The system of claim 5, wherein said first magnetic field sensor is electrically coupled with said transmission line.

10. The system of claim 5, wherein said first magnetic field is said second magnetic field.

11. A method for assessing interference to a first signal within a transmission line, the interference caused by a magnetic field, comprising:
 generating, by a magnetic field sensor, a second signal representative of said magnetic field as detected by said magnetic field sensor;
 receiving, by a processor, said second signal;
 processing, by said processor, said second signal to determine whether said magnetic field may cause distortion to said first signal within said transmission line; and
 determining, by said processor, a magnitude of distortion likely to be caused to said first signal by said magnetic field detected by said magnetic field sensor.

12. The method of claim 11, wherein said processing step comprises the substep of comparing said magnetic field as detected by said magnetic field sensor to a predetermined magnetic field threshold value.

13. The method of claim 11 further comprising the steps of:
 generating a third signal representative of certain information relating to said magnetic field detected by said magnetic field sensor; and
 displaying, on a display device, said information represented by said third signal.

14. The method of claim 11, wherein said determining step comprises the substeps of:
 receiving, by said processor, said first signal; and
 processing said first and second signals together to determine said magnitude of distortion.

15. The method of claim 11 further comprising filtering said first signal to compensate for the distortion caused by said magnetic field.

\* \* \* \* \*